(12) United States Patent
Liu et al.

(10) Patent No.: US 10,314,727 B2
(45) Date of Patent: Jun. 11, 2019

(54) OCCLUDER AND OCCLUSION DEVICE

(71) Applicant: Lifetech Scientific (Shenzhen) Co., Ltd., Shenzhen (CN)

(72) Inventors: Xiangdong Liu, Shenzhen (CN); Xianmiao Chen, Shenzhen (CN); Xiang Fu, Shenzhen (CN); Jie Chen, Shenzhen (CN)

(73) Assignee: Lifetech Scientific (Shenzhen) Co. Ltd., Shenzhen (CN)

( * ) Notice: Subject to any disclaimer, the term of this patent is extended or adjusted under 35 U.S.C. 154(b) by 79 days.

(21) Appl. No.: 15/322,669

(22) PCT Filed: Jul. 3, 2015

(86) PCT No.: PCT/CN2015/083292
§ 371 (c)(1),
(2) Date: Dec. 28, 2016

(87) PCT Pub. No.: WO2016/000661
PCT Pub. Date: Jan. 7, 2016

(65) Prior Publication Data
US 2017/0156904 A1    Jun. 8, 2017

(30) Foreign Application Priority Data
Jul. 4, 2014    (CN) .......................... 2014 1 0318632

(51) Int. Cl.
*A61F 2/94* (2013.01)
*A61B 17/00* (2006.01)
(Continued)

(52) U.S. Cl.
CPC ............... *A61F 2/94* (2013.01); *A61B 17/00* (2013.01); *A61B 17/0057* (2013.01);
(Continued)

(58) Field of Classification Search
CPC .......... A61B 17/12022; A61B 17/0057; A61B 2017/00619; A61B 2017/00606; A61B 2017/00623; A61F 2002/9505
(Continued)

(56) References Cited

U.S. PATENT DOCUMENTS

2002/0169473 A1* 11/2002 Sepetka ........... A61B 17/12022
606/200
2005/0273135 A1   12/2005 Chanduszko et al.
(Continued)

FOREIGN PATENT DOCUMENTS

CN          1224999 A      8/1999
CN        101500494 A      8/2009
(Continued)

OTHER PUBLICATIONS

International Search Report dated Jul. 29, 2015 for PCT/CN2015/083292.
(Continued)

*Primary Examiner* — Eric J Rosen
*Assistant Examiner* — Chima U Igboko
(74) *Attorney, Agent, or Firm* — Raymond Sun

(57) ABSTRACT

The present invention relates to an occluder, comprising a meshed occlusion body provided with a cavity, and a proximal hub, as well as a locking member and a stopping member both of which are located in the cavity. The distal end of the locking member is connected to the distal end of the occlusion body. The stopping member is disposed at the proximal end of the locking member. The proximal occluder head is provided with a locking hole in communication with the cavity. An occlusion device comprises the occluder, a hollow delivery' mechanism and a traction member. The distal end of the traction member is detachably connected to the proximal end of the locking member of the occluder after
(Continued)

extending through the distal end of the delivery' mechanism. The occlusion device has a simple locking structure, and simplifies the manufacturing process and the locking operation.

8 Claims, 8 Drawing Sheets

(51) Int. Cl.
*A61F 2/02* (2006.01)
*A61F 2/86* (2013.01)
*A61F 2/966* (2013.01)
*A61B 17/12* (2006.01)
*A61F 2/95* (2013.01)

(52) U.S. Cl.
CPC .......... *A61B 17/12168* (2013.01); *A61F 2/02* (2013.01); *A61F 2/86* (2013.01); *A61F 2/966* (2013.01); *A61B 17/12172* (2013.01); *A61B 2017/00606* (2013.01); *A61B 2017/00619* (2013.01); *A61B 2017/00623* (2013.01); *A61B 2017/12095* (2013.01); *A61F 2002/9505* (2013.01)

(58) Field of Classification Search
USPC ........................................................ 606/213
See application file for complete search history.

(56) References Cited

U.S. PATENT DOCUMENTS

| | | | |
|---|---|---|---|
| 2005/0288786 A1* | 12/2005 | Chanduszko | A61B 17/0057 623/11.11 |
| 2007/0118176 A1 | 5/2007 | Opolski | |
| 2010/0185233 A1* | 7/2010 | Thommen | A61B 17/0057 606/213 |
| 2011/0082495 A1 | 4/2011 | Ruiz | |
| 2012/0172927 A1 | 7/2012 | Campbell | |
| 2013/0289618 A1* | 10/2013 | Chanduszko | A61B 17/0057 606/213 |

FOREIGN PATENT DOCUMENTS

| | | |
|---|---|---|
| CN | 103690202 | 4/2014 |
| CN | 203576563 U | 5/2014 |
| CN | 104116574 A | 10/2014 |
| CN | 204133533 U | 2/2015 |
| EP | 1891902 | 2/2008 |
| WO | WO 02/069783 | 9/2002 |
| WO | WO 2005/110240 | 11/2005 |
| WO | WO 2005110240 | 11/2005 |

OTHER PUBLICATIONS

Office Action for corresponding European Application No. 15 816 064.8.
First Office Action for corresponding China Application No. 201410566309.7.
Second Office Action for corresponding China Application No. 201410566309.7.

* cited by examiner

OCCLUDER AND OCCLUSION DEVICE

TECHNICAL FIELD

The present invention relates to an interventional medical device, and more particularly to an occluder and occlusion device for the interventional treatment of congenital heart defect.

BACKGROUND ART

Percutaneous interventional technology is a rapidly developed means of disease treatment in recent years, and its application range is becoming wider and wider. A variety of materials, devices and drugs can be placed into heart, artery and vein blood vessels of a human body by using catheter interventional therapy, wherein the devices may be heart defect occluders, vascular plugs, vascular filters, etc.

The transcatheter interventional occluder is a commonly used device in transcatheter interventional therapy and can be used for the minimally invasive treatment of such congenital heart diseases as atrial septal defects and ventricular septal defects, patent ductus arteriosus and patent foramen ovale. An occluder in the prior art typically comprises an occlusion body having two occlusion units, for covering the tissue of the two sidewalls of the defect site. However, at present, the occlusion unit is, more often than not, prepared from shape memory metals or polymer materials. The shape memory metals may cause fatigue failure in use, while the polymer materials have the characteristics of low elasticity or inelasticity, which will lead to insufficient contraction force between the two occlusion units as well as the inability of fitting either side of the defect site, thereby affecting the occluding effect. Therefore, the occluder needs an effective restraining structure to keep the distance between the two occlusion units (namely, the waist height of the occluder) stable to ensure the reliability of the occlusion.

SUMMARY OF THE INVENTION

The technical problem to be solved by the present invention is to provide an occluder and an occlusion device with a locking function in view of the drawbacks of the prior art.

The technical solution of the present invention for solving the technical problem is as follows: an occluder comprises a meshed occlusion body provided with a cavity, and a proximal hub, and further comprising a locking member and a stopping member both of which are disposed in the cavity, wherein a distal end of the locking member is connected with a distal end of the occlusion body, and the stopping member is disposed at a proximal end of the locking member; and the proximal hub is provided with a locking hole extending through the cavity, a radial size of the stopping member is slightly larger than an aperture of the locking hole, a radial size of the locking member is smaller than an aperture of the locking hole, and at least one of the proximal hub and the stopping member is an elastic member.

In an embodiment of the present invention, a proximal end surface of the proximal hub of the occluder is provided with an accommodating groove with an internal diameter larger than the aperture of a proximal end port of the locking hole, and the locking hole is coupled with the accommodating groove to form a step-like through hole.

In an embodiment of the present invention, in the occluder, at least one of a distal end port and the proximal end port of the locking hole is expanded outwards to have a flared shape; or the aperture of the distal end of the locking hole is larger than the aperture of the proximal end, and the locking hole is in a frustum shape.

In an embodiment of the present invention, in the occluder, the occluder comprises a plurality of stopping members which are disposed in a spaced-apart manner, and a distance between two adjacent stopping members is larger than an axial length of the locking hole.

In an embodiment of the present invention, in the occluder, the wall of the locking hole is provided with an expansion joint from the proximal end along the axial direction.

In an embodiment of the present invention, in the occluder, the occlusion body is made from a polymer material capable of being biocompatible with the human body.

In an embodiment of the present invention, in the occluder, the proximal end of the locking member is provided with a threaded blind hole.

An occlusion device comprises the above-mentioned occluder, a hollow delivery mechanism with at least the distal end open, and a traction member movably accommodated in the delivery mechanism, wherein the distal end of the traction member is detachably connected with the proximal end of the locking member in the cavity after extending through the distal end of the delivery mechanism; the traction member is used for pulling the locking member such that the stopping member passes through the locking hole and presses against the proximal hub to lock the occluder.

In an embodiment of the present invention, in the occlusion device, the distal end of the traction member is provided with external threads matched with the threaded blind hole in the proximal end of the locking member.

In an embodiment of the present invention, in the occlusion device, the proximal end of the locking member is provided with a connecting ring; and the traction member comprises a traction wire that is surrounded by the connecting ring.

In an embodiment of the present invention, in the occlusion device, the distal end of the delivery mechanism is provided with a groove body for accommodating the stopping members.

In the occluder of the present invention, a locking process may be carried out with a locking member and a stopping member being coupled with a proximal hub having a locking hole; with a simple structure, the occluder simplifies the preparation process and locking operation. Moreover, the stopping members with slightly larger radial size press against the end face of the proximal hub to achieve locking, the locking reliability is high, and occurrences of locking failure are minimized. At least one of the proximal hub and the stopping member is an elastic member, the stopping members with slightly larger radial size pass through the locking hole by elastic deformations, which is a reversible operating process, and both the locking process and the withdrawing process are simple and easy.

In the occlusion device of the present invention, the traction member is detachably connected to the locking member of the above-mentioned occluder, the traction member is able to facilitate controlling the connection or releasing the connection, which increases the operability of the connection of the traction member and the occluder, and after the locking is completed, the occlusion device can be released from the connection and be evacuated out of the body, thereby reducing residues in vivo. Meanwhile, the traction member is not required to pass through the distal end of the occluder, which can avoid damage to cardiac tissues, reduce the time of an occlusion procedure, and increase the efficiency of an operation at the same time. Moreover, as the locking member is only fixed with the distal end of the occlusion body and the placement direction of the locking member is the same as that of the sheathing tube, the structure and the fixing mode of the locking member do not affect the deformation of the occluder in the delivery sheath tube and the occlusion to the defect site after the occluder is pushed in place. The size of the sheath tube only needs to fit the size of the occluder. In addition, since the size of the sheathing tube is not increased, this is more beneficial for the surgical procedure.

BRIEF DESCRIPTION OF THE DRAWINGS

In the following, the present invention will be further described by way of the appended drawings and the embodiments, and in the drawings.

DETAILED DESCRIPTION OF THE INVENTION in order to have a clearer understanding of the technical features and effects of the present invention, the present invention now will be described more fully hereinafter with reference to the accompanying drawings.

In order to describe the structure of the present invention more clearly, the terms "distal end" and "proximal end" are used as positional terms, the positional terms are the conventional terms in the field of interventional medical devices, wherein the "distal end" represents one end which is far away from the operator during the surgical procedure, and the "proximal end" represents one end which is closer to the operator during the surgical procedure. The axial direction refers to the direction parallel to the connecting line of the distal center and the proximal center of the medical device; and the radial direction refers to the direction perpendicular to the above mentioned axial direction.

Figure 1:
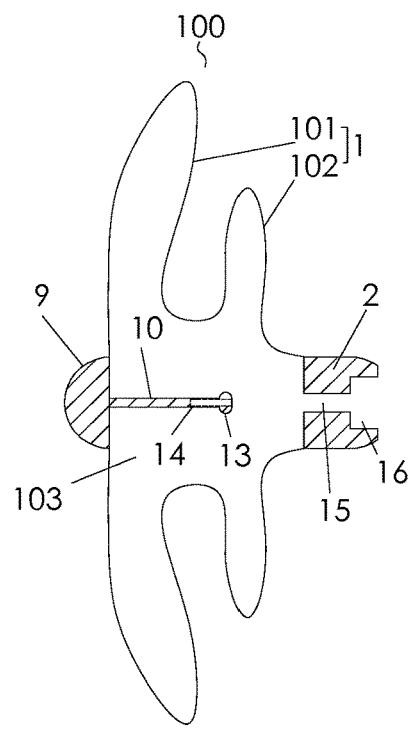
FIG. 1 is a schematic diagram of the occluder according to a first embodiment of the present invention.
Figure 2:
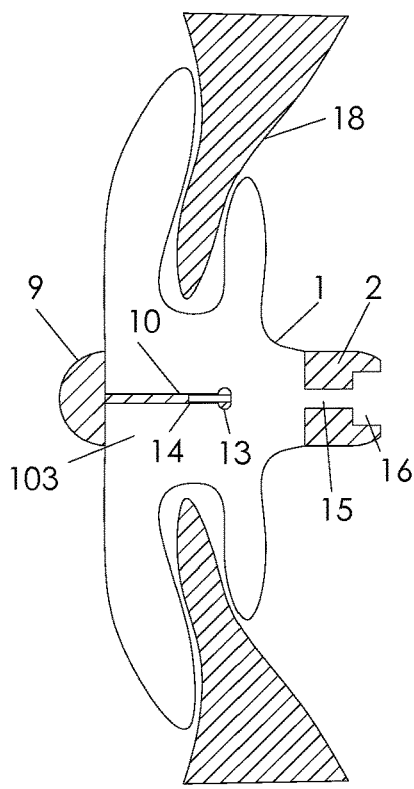
FIG. 2 is a schematic diagram of the occluder in a free state when it is unlocked according to the first embodiment of the present invention.
Figure 3:
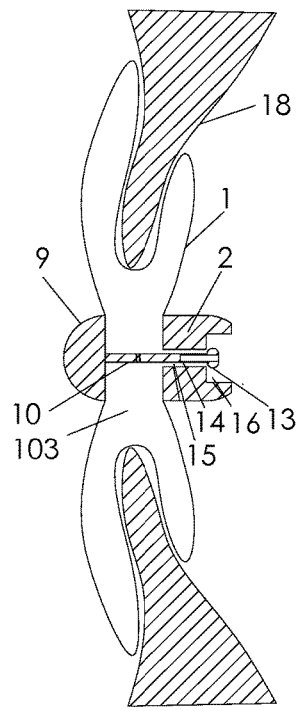
FIG. 3 is a schematic diagram of the occluder in a locking state according to the first embodiment of the present invention.

In the first embodiment, as shown in FIGS. 1-3, the occluder 100 comprises a meshed occlusion body 1 provided with a cavity 103, and a proximal hub 2. The occluder 100 further comprises a locking member 10 and a stopping member 13 both of which are disposed in the cavity 103, wherein the distal end of the locking member 10 is connected with a distal end of the occlusion body 1, and the stopping member 13 is disposed at a proximal end of the locking member 10. The proximal hub 2 is provided with a locking hole 15 penetrating through the cavity 103. The radial size of the stopping member 13 is slightly larger than an aperture of the locking hole 15. The radial size of the locking member 10 is smaller than an aperture of the locking hole 15, and at least one of the proximal hub 2 and the stopping member 13 is an elastic member. The elastic member can undergo resilient deformation under external force, and can completely recover from the deformation after the external force disappears.

The occluder 100 can assume a locking state, under the traction of an external force. The locking member 10 drives the distal end of the occlusion body 1 and the stopping member 13 to move toward the proximal hub 2, until the stopping member 13 passes through the locking hole 15 and presses against the end surface of the proximal hub 2 to lock the occlusion body 1. The external force can be the traction that the surgeon applies on the traction member toward the proximal end. The distance between the proximal end surface and the distal end surface of the occlusion body 1 is constant in the locking state (i.e. the waist height of the occlusion body is constant).

The free state of the occluder 100 when it is unlocked is shown in FIG. 1. The unlocked state of the occluder 100 being released after reaching the defect site 18 is shown in FIG. 2. FIG. 3 shows the occluder 100 occluding the defect site 18 in the locked state.

As shown in FIGS. 1-3, the occlusion body 1 has a meshed structure, which is provided with a cavity 103. For example, the occlusion body 1 with meshed structure comprises two occlusion units 101 and 102, both with a disc-like structure, wherein the two occlusion units 101 and 102 are connected to form an "I" shape. The structure of the occlusion body is only used for illustration, rather than limiting the present invention, as those skilled in the art can select any suitable structure for the occlusion body 1 using the principles of the present invention. As the meshed structure is susceptible to deformation, the occluder 100 can be compressed into the sheath tube effectively during delivery, and also can deform into two disc-like structures beneficial for occluding the defect when it is pushed out of the sheath tube at the defect site 18.

The meshed structure of the occlusion body 1 may be made from a shape memory alloy material or a polymer material by way of braiding, pipe cutting, injection molding or the like. The shape memory alloy material includes Ni—Ti alloy. The polymer material has good biocompatibility, and in contrast with metal materials, the polymer material is capable of avoiding problems caused by in vivo release of metal elements. In addition, the material having good biocompatibility is capable of effectively reducing infections at the occlusion site. The occlusion body 1 in the present invention may be braided from degradable polymer threads that may be selected from such similar materials as PET (Polyethylene Terephthalate). PLA (Poly-L-lactide Acid). PGA (Poly-Glycolide). PHA (poly-Hydroxyalkanoate). PDO (Poly-dioxanone), and PCL (Poly-caprolactone).

As shown in FIGS. 1-3, the distal end of the occlusion body 1 is further provided with a distal occlusion head 9 to which the locking member 10 is connected. In addition, the distal end of the occlusion body 1 may also be configured as a structure without an occlusion head. In the case of the occluder 100 of the structure without an occlusion head at the distal end, the locking member 10 may be directly connected to the distal end of the occlusion body 1. In the case of the occlusion body 1 of the meshed structure made from braiding threads, the distal occlusion head 9 and the proximal hub 2 may be disposed at the distal end and the proximal end, respectively, in order to receive and fix the end portions of the braiding threads forming the meshed structure. No special limitations are made to the shapes and structures of the distal occlusion head 9 and the proximal hub 2. In this embodiment, the distal occlusion head 9 is a cambered-surface body, while the proximal hub 2 is of a cylindrical structure.

However, the shape memory alloy may lose efficacy and fail to effectively occlude the defect sites due to fatigue during long-term use. In addition, the polymer material, compared with the traditional memory alloy (e.g., Ni—Ti alloy), has the characteristics of lower elastic modulus and smaller elastic range. The above two materials may possibly result in a failure to maintain the preset form of the occlusion body 1 after setting. In this case, a locking structure is required to improve the stability of the occluder 100 in a human body. The locking structure thus is correspondingly designed in the present invention, which is applicable to locking both the occlusion body 1 made from the polymer material and occluders 100 made from other materials.

The locking function of the occluder 100 is mainly realized by the locking member 10 and the stopping member 13 both disposed in the cavity 103 of the occlusion body 1 in cooperation with the locking hole 15 formed in the proximal hub 2. The locking member 10 may be of a cylindrical structure, a rod-like structure or a thread-like structure, with the cross section thereof being either circular or elliptical. The locking member 10 may be made from a metal material or a biocompatible polymer material, and thus can be a metal wire or a thin metal slender in this embodiment. The distal end of the locking member 10 is connected to the distal end of the occlusion body 1 such that the locking member 10 may drive the distal end of the occlusion body 1 to move toward the proximal end thereof under the traction of an external force (e.g., the pull of the traction member).

The stopping member 13 is disposed at the proximal end of the locking member 10, and used for connection with an external pusher; therefore, the proximal end of the locking member 10 corresponds to the locking hole 15 in the proximal hub 2. The locking member 10 may be disposed coaxially with the locking hole 15 so as to move linearly such that the stopping member 13 enters the locking hole 15 smoothly. In order to guarantee effective locking of the occluder, the locking length of the locking member 10. i.e., the distance between the end face of the distal end of the locking member 10 and the stopping member 13, is required to be less than the total height of the occluder 100 and equal to or slightly less than the height of a heart defect site to be occluded. "The total height of the occluder" represents the distance between the distal end of the occlusion body 1 and the proximal end of the occlusion body 1 when the occluder 100 is in a free state or relaxed state before being released. When the stopping member 13 presses against the end face of the proximal hub 2 to complete locking, locking takes effect with the locking length less than the total height of the occluder 100; therefore, two occlusion units may fit the defect site more closely and then the occluder 100 completely occludes the defect tissue. If the stopping member 13 retracts into the occlusion body 1, the locking fails, resulting in the unlocking of the occluder 100.

Figure 4:
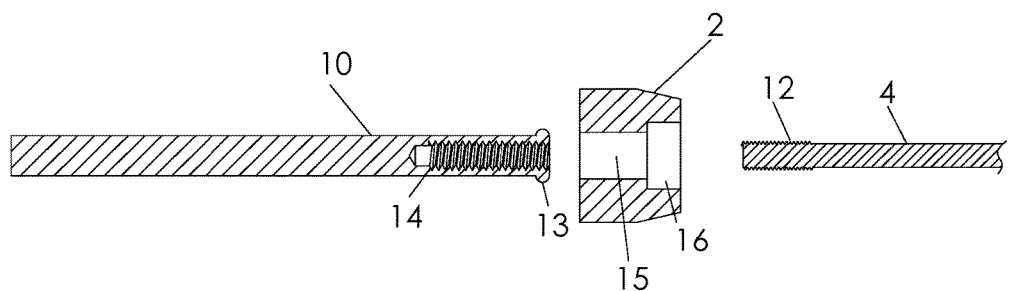
FIG. 4 illustrates the cooperation of the locking member with the proximal hub and the traction member according to the first embodiment 1 of the present invention.

With reference to FIG. 4, as the locking member 10 is required to be detachably connected with the pusher, a threaded connection can be utilized as one detachable connection mode. A threaded blind hole 14 may be formed in the proximal end of the locking member 10, which corresponds to the traction member 4 with external threads 12. The traction member 4 is threadably connected with the threaded blind hole 14 in the proximal end of the locking member 10 to achieve a detachable connection between the traction member 4 and the occluder 100. Moreover, the traction member 4 and the locking member 10 can be separated only by turning the traction member 4 in vitro during release, and the reliability and operability of the connection between the traction member 4 and the occluder 100 are improved. Meanwhile, the distal end of the occluder 100 does not need to be penetrated through, so that damage to cardiac tissues can be avoided.

As shown in FIGS. 1-5, the stopping member 13 is disposed at the proximal end of the locking member 10. The stopping member 13 may be either directly disposed on the outer wall of the proximal end of the locking member 10, or independently molded and fixedly connected to the proximal end of the locking member 10; alternatively, the stopping member 13 and the locking member 10 may form an integrated body and molding, or independently molded and then fixedly connected thereto. The stopping member 13 is not limited in shape. When disposed on the outer wall of the proximal end of the locking member 10, the stopping member 13 may be an annular flange circumferentially surrounding the outer wall of the locking member 10, or through the use of one or more projections. In the case of a plurality of projections, these projections may be circumferentially disposed at even intervals around the outer wall of the locking member 10.

As the radial size of the stopping member 13 is slightly larger than the aperture of the locking hole 15, at least one of the proximal hub 2 and the stopping member 13 is required to be an elastic member to allow the stopping member 13 to pass through the locking hole 15. Specifically, the elastic member undergoes elastic deformation under the external force to enable the stopping member 13 to enter the locking hole 15 and extend out of the proximal end of the locking hole 15. After the stopping member 13 extends out of the locking hole 15, the elastic member recovers to its original state so that the stopping member 13 cannot retract into the locking hole 15 without external force and presses against the end face of the proximal hub 2, so that the stopping member 13 is locked, thereby achieving an axial restraining. However, the radial size of the locking member 10 is smaller than the aperture of the locking hole 15 such that the locking member 10 can go into and out of the locking hole 15 smoothly.

The selection of the elastic member has no special limits; in the embodiment, at least one of the proximal hub 2 and the stopping member 13 is made from elastic metal or a elastic polymer material. For example, the elastic metal is elastic stainless steel or nickel-titanium alloy; for example, the elastic polymer material is polylactic acid or nylon. Generally, the proximal hub 2 is made from the polymer material, and the polymer material has a certain elasticity and can meet the elastic deformation amounts required by the stopping members 13 for entering the locking hole 15. Therefore, the proximal hub 2 may be an elastic member, and the stopping members 13 may be rigid members made from a hard material.

In the occluder, the locking member 10 and the stopping members 13 are operate with the proximal hub 2 provided with the locking hole 15 to complete the locking process. The locking member 10 is of rod-like or similar structure, and the stopping members 13 are protruding structures opposite to the locking member 10. Hence, the locking structure of the present invention is simple. No complicated mechanical structure and matching relations are needed. The manufacturing process and locking operation are simplified. Moreover, the stopping members 13 with slightly larger radial sizes press against the end face of the proximal hub 2 to achieve locking, so the locking reliability is high, and locking failure does not easily occur. At least one of the proximal hub 2 and the stopping member 13 is an elastic member, the stopping member 13 with slightly larger radial sizes passes through the locking hole 15 by elastic deformations, and the operation process is reversible. Both the locking process and the withdrawing process are simple and easy to carry out.

Figure 5:
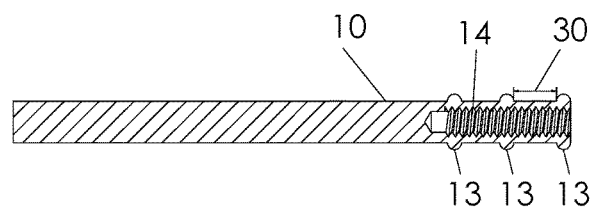
FIG. 5 is a schematic diagram of another implementation of the stopping member according to the first embodiment of the present invention.

As shown in FIG. 5, for correspondingly meeting different locking length requirements, the occluder 100 can be provided with multiple stopping members 13 disposed at intervals so that the stopping members 13 to be locked can be selected according to the heights of actual cardiac defects required to be occluded so as to adjust the effective locking length of the occluder 100. The spacing 30 between every two adjacent stopping members 13 is larger than the axial length of the locking hole 15, so that the other adjacent stopping member 13 at the distal end is located outside the distal end port of the locking hole 15 when one stopping member 13 presses against the proximal end face of the proximal hub 2. Therefore, the adjacent stopping members 13 are not mutually affected. When it is in the locking state, other stopping members are prevented from being locked in the locking hole, and so this avoids the phenomenon that the stopping members 13 and the elastic member in the locking hole 15 are difficult to restore due to long-term deformations and thus low locking reliability.

Figure 6:
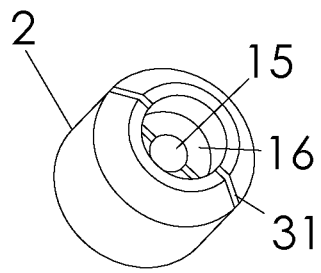
FIG. 6 is a perspective view of an implementation of the proximal hub according to the first embodiment of the present invention.

As shown in FIG. 6, to allow the stopping members to pass through the locking hole 15 in the locking operation process, for example, the hole wall of the locking hole 15 at the proximal hub 2 is provided with expansion joints 31 from the proximal end along the axial direction. When the stopping member 13 enters the locking hole 15, the expansion joint 31 is open to allow the stopping member 13 to pass through the locking hole 15 smoothly and then recovers to its original state. The expansion joints 31 are generally provided in a number of 2 to 4, and may be disposed symmetrically in an axial mode. The depth of the expansion joint 31 does not exceed the axial dimension of the proximal hub 2. In addition, the opening positions of the expansion joints 31 are located at the proximal end face of the proximal hub 2.

As shown in FIGS. 1 to 4, a proximal end face of the proximal hub 2 is provided with an accommodating groove 16 with a internal diameter of larger than the aperture of a proximal end port of the locking hole 15, and the locking hole 15 is cooperated with the accommodating groove 16 to form a step-like through hole. The stopping members 13 pass through the locking hole 15 to lock the occluder 100 and then are positioned in the accommodating groove 16 to avoid impacting the interaction between the delivery mechanism and the proximal hub 2. For example, when the delivery mechanism is used for pushing the proximal hub 2 to release the occluder 100, the delivery mechanism presses against the proximal end face of the proximal hub 2 so as to prevent the stopping members 13 from affecting the pushing action. The "internal diameter" herein refers to the spacing of the inner walls of the accommodating groove 16. For the same accommodating groove, the internal diameter refers to minimum spacing when the spacing of the opposite inner walls is different. The accommodating groove 16 is not limited in shape, which may be a square groove, or a cylindrical groove or an amorphous-structure groove, and only the locking hole 15 needs to be completely communicated with the accommodating groove 16. In addition, the depth of the accommodating groove 16 should completely accommodate the stopping members 13.

Figure 18:
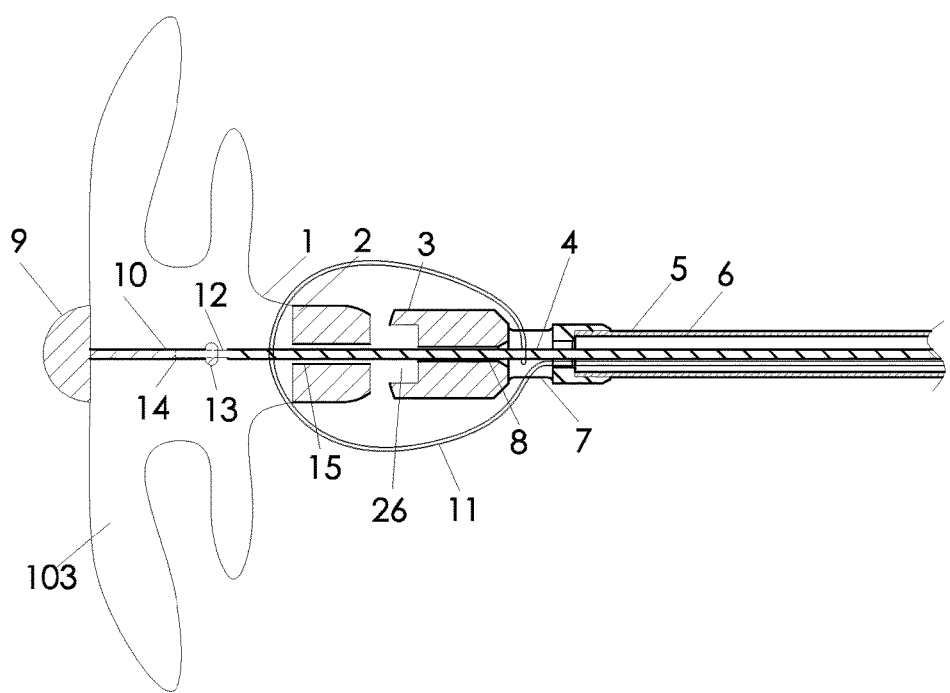
FIG. 18 is a schematic diagram showing the cooperation of the occluder with the delivery mechanism according to the second embodiment of the present invention.

As shown in FIG. 18, if the distal end of the delivery mechanism is also provided with a groove body 26 for accommodating the stopping members 13, it is possible to omit the accommodating groove 16, or the accommodating groove 16 is not needed to completely accommodate the stopping members 13 in depth, and the accommodating groove 16 can be cooperated with the groove body 26 at the distal end of the delivery mechanism to completely accommodate the stopping members 13.

Figure 7:
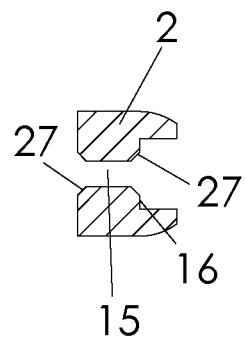
FIG. 7 is a sectional view of another implementation of the proximal hub according to the first embodiment of the present invention.
Figure 8:
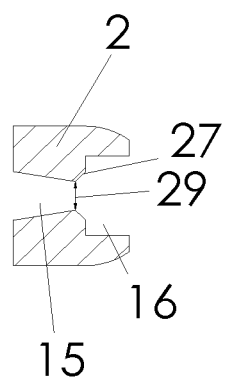
FIG. 8 is a sectional view of yet another implementation of the proximal hub according to the first embodiment of the present invention.

As shown in FIGS. 7 and 8, the locking hole 15 of the proximal hub 2 may also have various shapes. To allow the stopping members 13 to enter the locking hole 15 smoothly, as shown in FIG. 7, at least one of the distal end port and the proximal end port of the locking hole 15 is expanded outwardly to form a flare-shape, and the simple flare-shape refers to chamfers 27 that are respectively formed at two ends of the locking hole 15. The structure of the locking hole 15 of the proximal hub 2 is also as shown in FIG. 8, and the aperture of the distal end of the locking hole 15 is larger than the aperture of the proximal end, and the locking hole is in a frustum shape. In other words, the minimum radial size of the proximal end of the locking hole 15 is slightly larger than the radial size of the locking member 10 and meanwhile is smaller than the radial size of the stopping members 13 of the locking member 10. The flare-shaped ports and the frustum-shaped locking hole 15 can play a guiding role on the stopping members 13 and guide the locking member 10 to enter the locking hole 15. In addition, in the frustum-shaped locking hole 15, the proximal end aperture is kept smaller than the radial size of the stopping members 13, and the distal end port dimension of the locking hole 15 may be smaller than the radial size of the stopping members 13 or not. For example, a chamfer 27 may be formed in the proximal end port of the frustum-shaped locking hole 15 to facilitate retraction of the stopping member 13 from the locking hole 15 to the cavity 10 of the occluder 100 during the withdrawal of the occluder.

Figure 9:
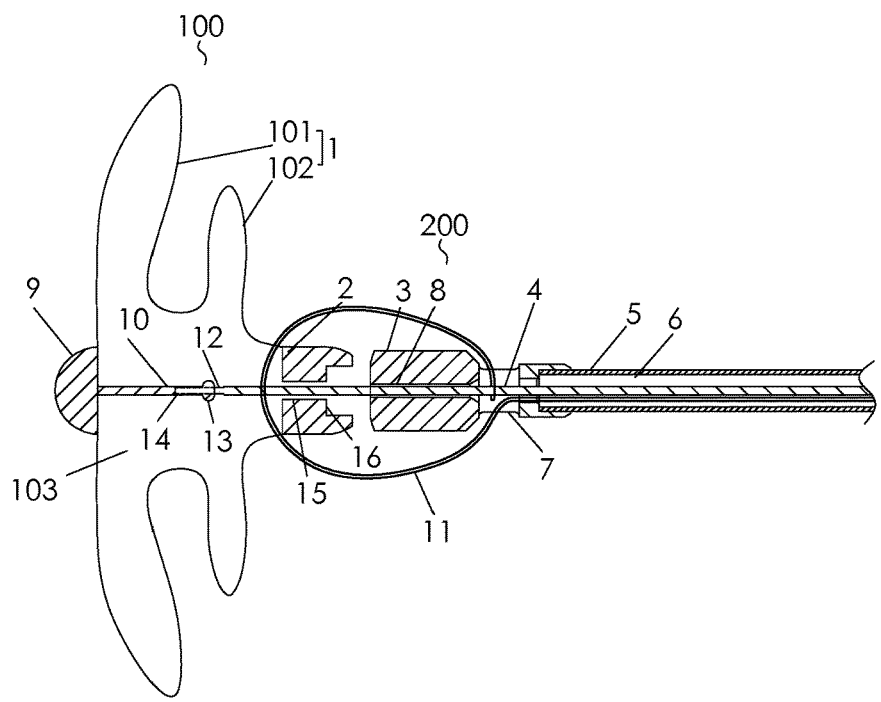
FIG. 9 is a schematic diagram of the occlusion device according to the second embodiment of the present invention.
Figure 9A:
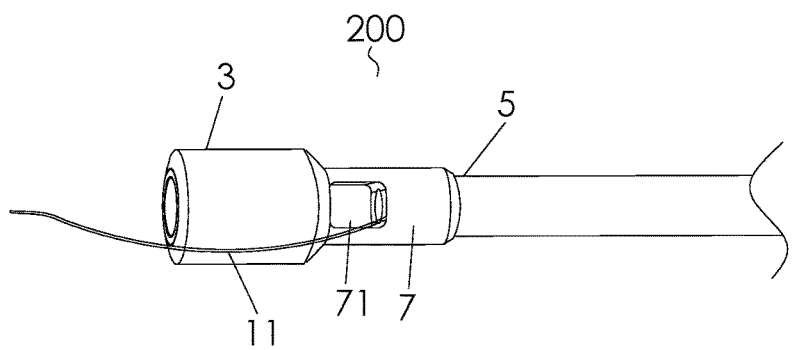
FIG. 9a is a schematic diagram of an implementation of the delivery mechanism according to the second embodiment of the present invention.

In the second embodiment, as shown in FIG. 9, the occlusion device comprises the occluder 100, a hollow delivery mechanism 200, and the traction member 4 movably accommodated in the delivery mechanism 200. The distal end of the traction member 4 extends through the distal end of the delivery mechanism 200 and is detachably connected with the proximal end of the locking member 10 in the cavity 103. The traction member 4 can utilize traction on the locking member 10 to drive the distal end of the occluder 100 to move towards the proximal end under external force by an operator, for example a surgeon, until the stopping members 13 extend through the locking hole 15 and then press against the end face of the proximal hub 2 to lock the occluder 100.

Figure 10:
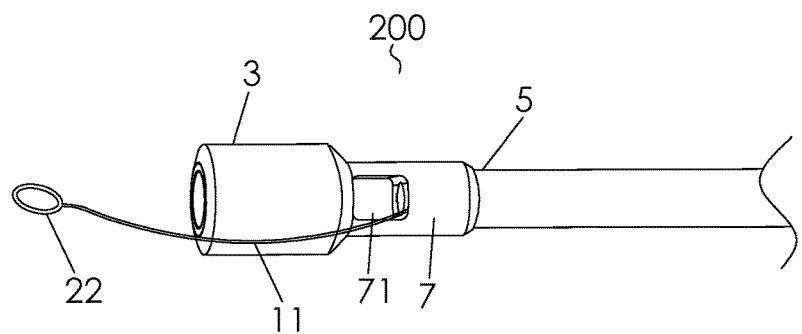
FIG. 10 is a schematic diagram of another implementation of the delivery mechanism according to the second embodiment of the present invention.

Referring to FIGS. 9 and 10, in one implementation, the hollow delivery mechanism 200 comprises a delivery tube 5, and the delivery tube 5 is axially provided with a lumen 6 that communicates with the outside at least at the distal end. A locking head 3 is disposed with respect to the distal end of the delivery tube 5 and is provided with a through hole 8 along the axial direction. The through hole 8 further communicates with the lumen 6 of the delivery tube 5 while extending through the distal end and the proximal end of the locking head 3. A locking tube 7 is disposed at the connecting position between the locking head 3 and the delivery tube 5 and is provided with a radial locking port 71. The locking port 71 simultaneously communicates with the lumen 6 of the delivery tube 5 and the through hole 8 formed in the locking head 3. The locking tube 7 can be in contact with a traction member 4 from the locking port 71. The locking tube 7 can be fixedly connected with the locking head 3 and can be also be integrated with the locking head 3. The distal end of the delivery tube 5 is surrounded by the locking tube 7 and is connected with the locking tube 7 through welding or a tight-fit, so that the locking tube 7 and the delivery tube 5 are fixedly connected together.

Figure 11:
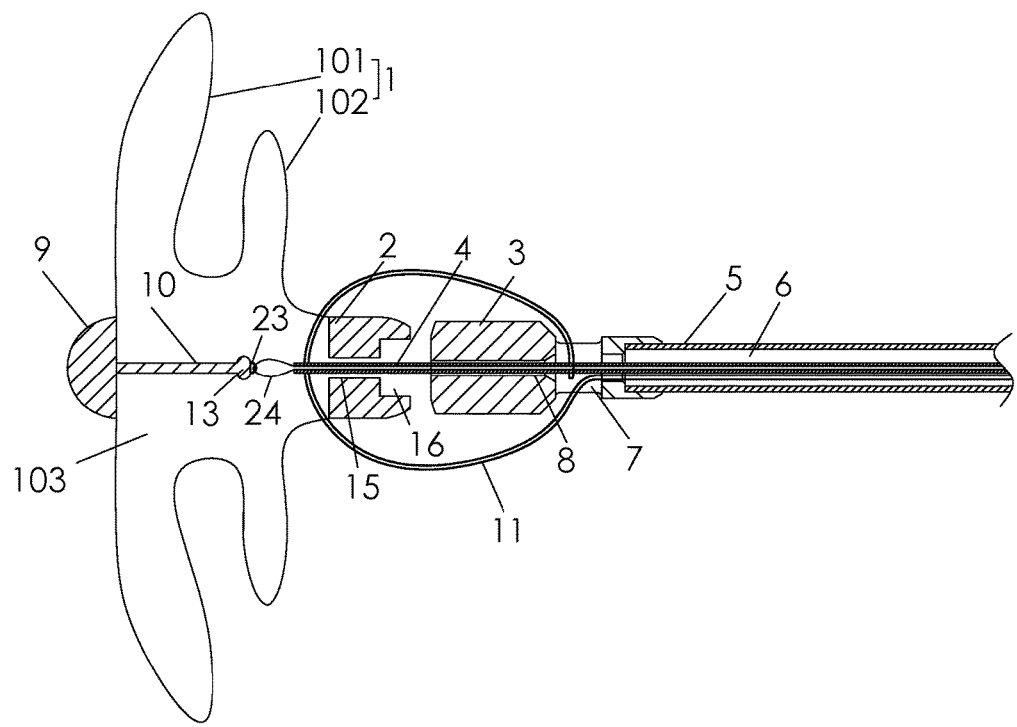
FIG. 11 is a schematic diagram of another detachable connection mode between the occluder and the traction member according to the second embodiment of the present invention.

As shown in FIGS. 9 and 11, the traction member 4 is accommodated in the through hole 8 of the locking head 3 and the lumen 6 of the delivery tube 5, and the traction member 4 can move axially along the through hole 8 and the lumen 6. The through hole 8 is coaxial with the lumen 6 of the delivery tube 5. The space between the traction member 4 and the delivery tube 5, and the space between the locking tube 7 and the locking head 3, do not affect the axial movement of the traction member 4, so the traction member 4 can move a certain axial distance.

In the present invention, the locking member 10 is detachably connected with the traction member 4. One detachable connection mode may be via a threaded connection, as shown in FIGS. 4 and 9. A threaded blind hole 14 is formed in the proximal end of the locking member 10. An external thread 12 is correspondingly disposed at the distal end of the rod-like traction member 4. The distal end of the traction member 4 is threadably connected with the threaded blind hole 14 formed in the proximal end of the locking member 10 to achieve a detachable connection between the traction member 4 and the occluder 100. Moreover, the traction member 4 and the locking member 10 can be separated only by turning the traction member 4 during release, so that the reliability and operability of the connection between the traction member 4 and the occluder 100 are improved. Meanwhile, it is not necessary to penetrate the distal end of the occluder 100 so that damage to cardiac tissues can be avoided.

Except the threaded connection mode, as shown in FIG. 11, the proximal end of the locking member 10 may be provided with a connecting ring 23. The traction member 4 further comprises a traction wire 24 that is surrounded by the connecting ring 23, and the traction wire 24 extends through the connecting ring 23 to connect the locking member 10 and the traction member 4 together. Specifically, the traction member 4 is provided with a through cavity along the axial direction, the traction wire 24 is disposed in the cavity of the traction member 4 and can move in the cavity along the axial direction, and one end of the traction wire 24 may extend through the connecting ring 23 and then may be folded back. After the occluder 100 is delivered in place, the locking member 10 is towed and locked by controlling the traction wire 24. After the locking is completed, the traction wire 24 can be withdrawn from the connecting ring 23 of the occluder 100 to thoroughly separate the occluder 100 from the traction member 4, so that no residue exists in the body.

The delivery mechanism 200 further comprises a connecting wire 11, and the delivery mechanism 200 is detachably connected with the occluder 100 through the connecting wire 11. As shown in FIGS. 9 and 10, in one embodiment, the connecting wire 11 is movably disposed in the lumen 6 of the delivery tube 5. The proximal end of the connecting wire 11 is controllable, namely the proximal end of the connecting wire 11 can extend out of the delivery mechanism 200 and then is directly controlled, or is connected with other control members to achieve control. The distal end of the connecting wire 11 extends out of the locking port 71, oppositely extends through a mesh of the occlusion body 1 of the occluder 100, and then enters the locking port 71 to be movably surrounded by the traction member 4 at the position. Except the above embodiments, a cyclic structure 22 is formed at the head of the single connecting wire 11, and the traction member 4 extends out of the cyclic structure 22. The cyclic structure 22 may be embodied in a variety of modes, for example, formed by knotting the head end of the connecting wire 11 or welding a metal ring at the head. After the occluder 100 and the delivery mechanism 200 are properly connected, it is ensured that the proximal hub 2 of the occluder 100 correctly faces the locking head 3 of the delivery mechanism 200 so that the locking head 3 can reliably press against the end face of the proximal hub 2 to push the occluder 100 out from a sheath tube. The distance between the occluder 100 and the locking head 3 can be adjusted by adjusting the length of the connecting wire 11. The connecting wire 11 may be a polymer wire, and may be also a multi-strand metal twisted wire, with a multi-strand nickel-titanium twisted wire adopted in this embodiment.

Figure 12:
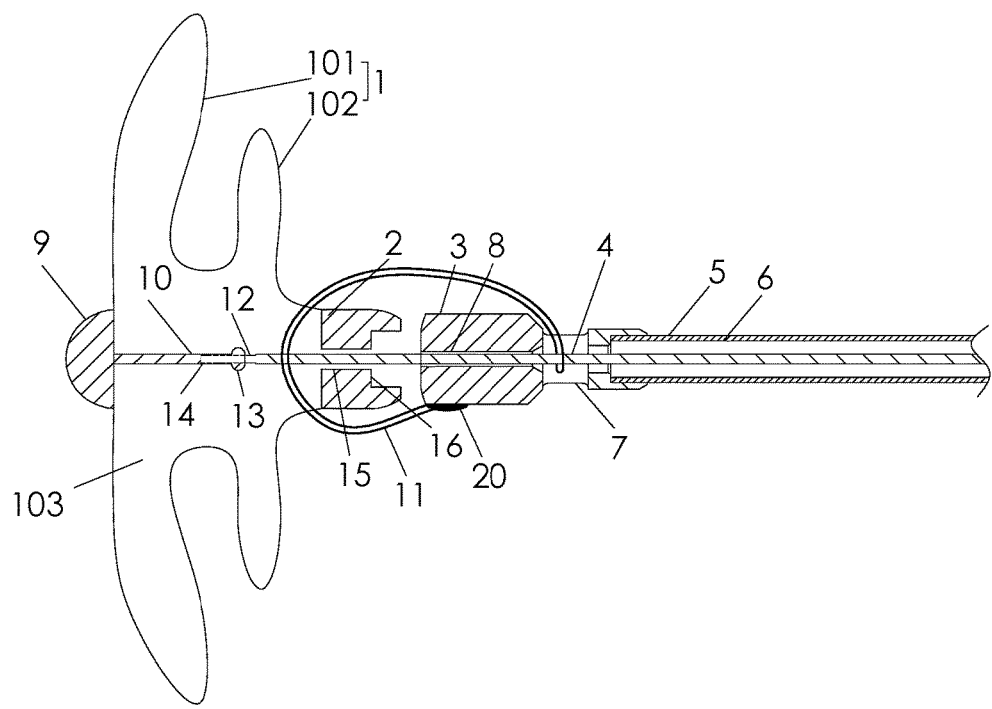
FIG. 12 is a schematic diagram of another implementation for fixing the connecting wire of the delivery mechanism according to the second embodiment of the present invention.

As shown in FIG. 12, in another embodiment, the difference is that the proximal end of the connecting wire 11 is fixed to the side wall of the locking head 3, and movement of the proximal end of the connecting wire 11 is controlled through the locking head 3. When the connecting wire 11 is a metal wire, the fixing mode can be a laser weld or a resistance weld. If the connecting wire 11 is a non-metal wire, the fixing mode can be an adhesive fixing mode. In FIG. 12, one end of the connecting wire 11 is fixed to a welding point or an adhesive point 20.

As shown in FIG. 18, the distal end of the delivery mechanism is provided with a groove body 26 for accommodating the stopping member 13. It can be seen that the groove body 26 is disposed at the distal end of the locking head 3 in the delivery mechanism, an accommodating groove 16 at the proximal hub 2 may be omitted, or the accommodating groove 16 is not needed to completely accommodate the stopping member 13 in depth, and the accommodating groove 16 can be operatively engaged with the groove body 26 at the distal end of the delivery mechanism to completely accommodate the stopping members 13. The groove body 26 at the opening of the distal end of the delivery mechanism provides an accommodating space for the locked stopping member 13, so that the complete shape and a smooth and continuous surface of the proximal end face of the proximal hub 2 can be ensured without changing the shape of the proximal hub 2 of the occluder 100, and thrombus formation can be minimized.

Figure 13:
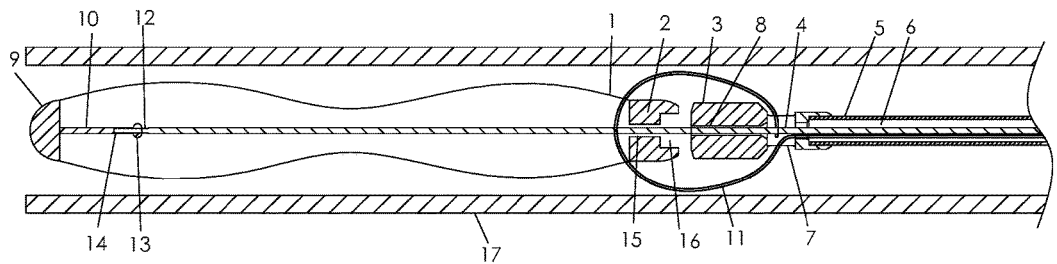
FIG. 13 is a schematic diagram showing the occluder located in the sheath tube according to the second embodiment of the present invention.

FIGS. 13 to 17 illustrate how the occluder 100 and the delivery mechanism 200 operate together to carry out the delivery, releasing and locking processes. As shown in FIG. 13, the occluder 100 and the delivery mechanism 200 are first connected together through the connecting wire 11 and are placed into the sheath tube 17. The distal end of the traction member 4 is in threaded connection with the locking member 10. When the occluder 100 is placed into the sheath tube 17, the traction member 4 is disposed in the axial direction of the sheath tube 17 without restraining free deformation of the occluder 100.

Figure 14:
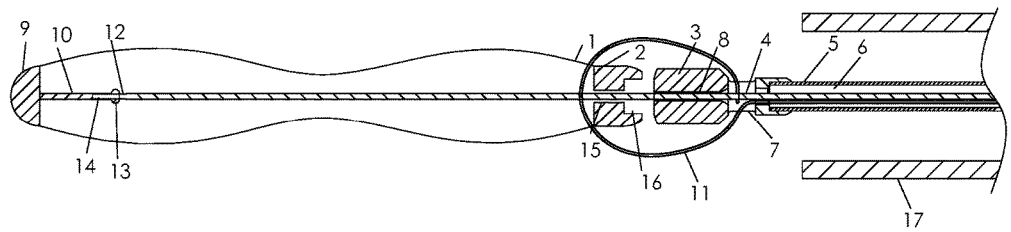
FIG. 14 is a schematic diagram showing the occluder being pushed out of the sheath tube in FIG. 13.

After it is positioned near the targeted lesion position, the delivery tube 5 is pushed, the distal end of the locking head 3 presses against the proximal hub 2 of the occluder 100 to move the occluder 100 forward, and finally, as shown in FIG. 14, the occluder 100 is pushed out of the sheath tube 17.

Figure 15:
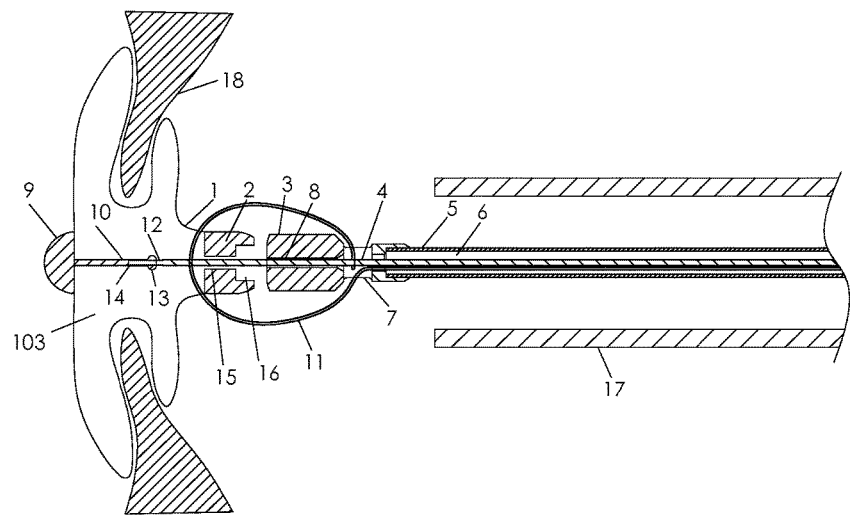
FIG. 15 is a schematic diagram showing the occluder being released but unlocked after reaching the defect site in FIG. 14.

The occluder 100 is pushed to a heart defect site 18, the traction member 4 is retracted, and the locking head 3 presses against the proximal hub 2 of the occluder 100, so that two disc-like structures of the occluder 100 are gradually drawn together to form an "I" shape as shown in FIG. 15.

Figure 16:
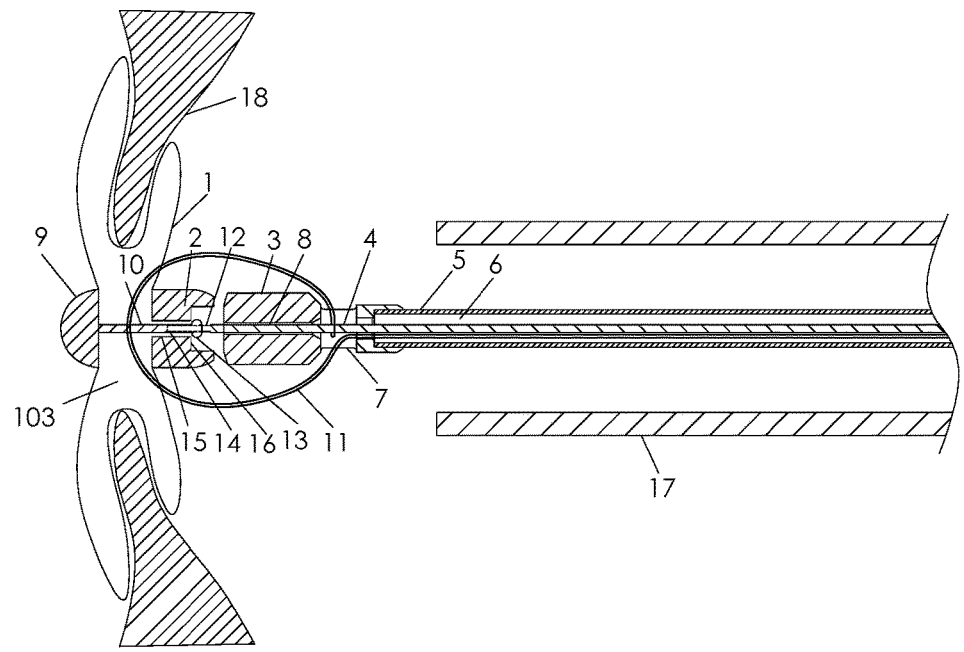
FIG. 16 is a schematic diagram showing the occluder of FIG. 15 after it has been locked.

Under the traction of the traction member 4, the locking member 10 and the stopping member 13 collectively press against a locking hole 15 of the proximal hub 2. The proximal hub 2 and the stopping member 13 experience a certain elastic deformation, so that the stopping member 13 can pass through the locking hole 15 and is unlikely to rebound along the axial direction after passing through the locking hole 15, thereby achieving an axial restraining effect. As shown in FIG. 16, when the stopping member 13 of the locking member 10 pushes against the end surface of the proximal hub 2, the occluder 100 is locked.

Figure 17:
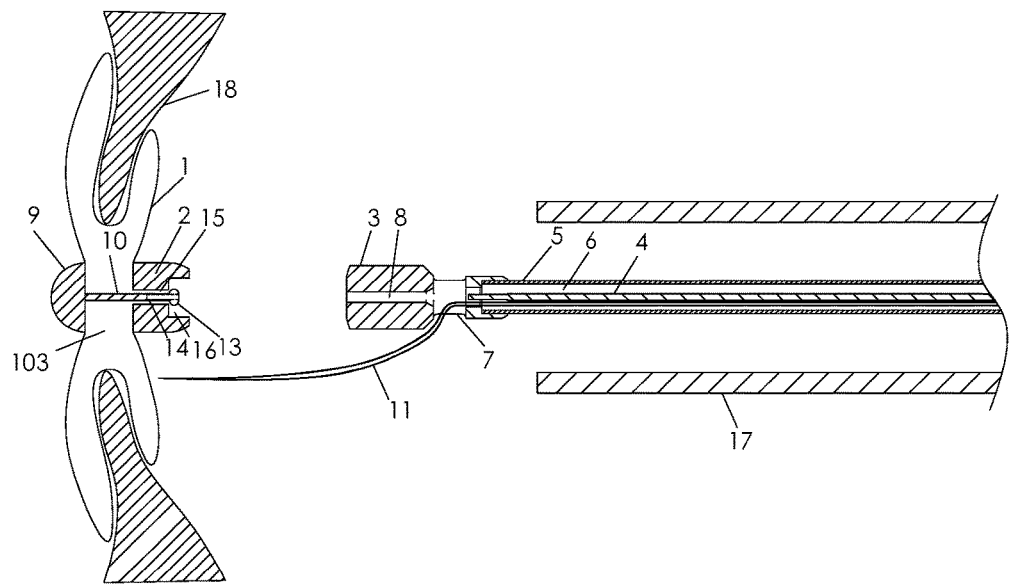
FIG. 17 is a schematic diagram showing the evacuation of the occluder and the delivery mechanism in FIG. 16.

As shown in FIG. 17, the traction member 4 is rotated to be disconnected with the locking member 10. The traction member 4 is retracted after the disconnection until the traction member 4 is disconnected from the connecting wire 11, and finally the delivery tube 5 is retracted so as to release the connection between the connecting wire 11 and the occluder 100.

The stopping member 13 passes through the locking hole 15 by means of the elastic deformation, so that the locking process is reversible. The occluder 100 further assumes an unlocking state. Before the connection between the traction member 4 and the locking member 10 is released, the delivery tube 5 can be operated along the axial direction, so that the traction member 4 is pushed forward until the stopping member 13 is returned into the cavity 103 of the occluder 100 through the locking hole 15, and the occluder 100 is unlocked, restored from the state as shown in FIG. 15 to the state as shown in FIG. 14; and after the occluder 100 is restored to the state as shown in FIG. 14, the delivery tube 5 can be further pulled towards the proximal end, so that the occluder 100 is retracted into the sheath tube 17, thereby recycling the occluder 100.

The invention claimed is:

1. An occluder comprising:
   a meshed occlusion body provided with a cavity, the occlusion body having a distal end;
   a proximal hub having a body;
   a locking member and a plurality of stopping members, wherein the locking member and each of the plurality of stopping members have a radial size and are disposed in the cavity, the locking member having a distal end and a proximal end, wherein the distal end of the locking member is connected with the distal end of the occlusion body, and the plurality of stopping members are disposed at the proximal end of the locking member;
   wherein the proximal hub is provided with a locking hole extending through the cavity, the locking hole having an aperture, with the radial size of the plurality of stopping members being larger than the aperture of the locking hole, and the radial size of the locking member is smaller than the aperture of the locking hole, and wherein the proximal hub is an elastic member and/or the plurality of stopping members are each an elastic member;
   wherein the locking hole further includes at least one expansion joint that extends along the body of the proximal hub along an axial direction, such that the at least one expansion joint opens when the plurality of stopping members pass through the locking hole, the proximal hub further having a proximal end face which is provided with an accommodating groove with an internal diameter that is larger than the aperture of the locking hole, and the locking hole is coupled with the accommodating groove to form a stepped through hole; and
   wherein each stopping member of the plurality of stopping members is disposed in a spaced-apart manner with a distance between adjacent stopping members that is larger than an axial length of the locking hole.

2. The occluder of claim 1, wherein the locking hole has a distal end port and a proximal end port, at least one of which is expanded outwardly to have a flared shape.

3. The occluder of claim 1, wherein the locking hole has a distal end and a proximal end, each of which has an aperture, and wherein the aperture of the distal end of the locking hole is larger than the aperture of the proximal end of the locking hole, and wherein the locking hole has a frustum shape.

4. The occluder of claim 1, wherein the occlusion body is made from a polymer material that is biocompatible with the human body.

5. The occluder of claim 1, wherein the proximal end of the locking member is provided with a threaded blind hole.

6. An occlusion device, which comprises;
   An occluder comprising:
   a meshed occlusion body provided with a cavity, the occlusion body having a distal end;
   a proximal hub having a body;
   a locking member and a stopping member, both of which have a radial size and are disposed in the cavity, the locking member having a distal end and a proximal end, wherein the distal end of the locking member is connected with the distal end of the occlusion body, and the stopping member is disposed at the proximal end of the locking member;

wherein the proximal hub is provided with a locking hole extending through the cavity, the locking hole having an aperture, with the radial size of the stopping member being larger than the aperture of the locking hole, and the radial size of the locking member is smaller than the aperture of the locking hole, and at least one of the proximal hub and the stopping member is an elastic member;

wherein the locking hole further includes at least one expansion joint that extends along the body of the proximal hub along an axial direction, such that the at least one expansion joint opens when the stopping member passes through the locking hole, the proximal hub further having a proximal end face which is provided with an accommodating groove with an internal diameter that is larger than the aperture of the locking hole, and the locking hole is coupled with the accommodating groove to form a stepped through hole;

a hollow delivery mechanism comprising:
  at least an open distal end, and
  a traction member movably accommodated in the delivery mechanism and having a distal end, wherein the distal end of the traction member is detachably connected with the proximal end of the locking member in the cavity after extending through the distal end of the delivery mechanism; and
  wherein the distal end of the delivery mechanism is provided with a groove body for accommodating the stopping member.

7. The occlusion device of claim 6, wherein the proximal end of the locking member is provided with a threaded blind hole, and the distal end of the traction member is provided with external threads that are matched with the threaded blind hole in the proximal end of the locking member.

8. The occlusion device of claim 6, wherein the proximal end of the locking member is provided with a connecting ring, and the traction member comprises a traction wire surrounded by the connecting ring.

* * * * *